(12) United States Patent
Jonsson et al.

(10) Patent No.: US 11,439,542 B2
(45) Date of Patent: *Sep. 13, 2022

(54) TAMPON APPLICATOR

(71) Applicant: Essity Hygiene and Health Aktiebolag, Gothenburg (SE)

(72) Inventors: Sylvia Jonsson, Gothenburg (SE); Conny Dahlqvist, Gothenburg (SE); Susanne Carlstedt, Malmö (SE); Malkus Arlemark, Malmö (SE)

(73) Assignee: ESSITY HYGIENE AND HEALTH AKTIEBOLAG, Gothenburg (SE)

( * ) Notice: Subject to any disclaimer, the term of this patent is extended or adjusted under 35 U.S.C. 154(b) by 0 days.

This patent is subject to a terminal disclaimer.

(21) Appl. No.: 16/652,228

(22) PCT Filed: Oct. 6, 2017

(86) PCT No.: PCT/EP2017/075541
§ 371 (c)(1),
(2) Date: Mar. 30, 2020

(87) PCT Pub. No.: WO2019/068349
PCT Pub. Date: Apr. 11, 2019

(65) Prior Publication Data
US 2020/0246197 A1 Aug. 6, 2020

(51) Int. Cl.
*A61F 13/26* (2006.01)
(52) U.S. Cl.
CPC .................................. *A61F 13/266* (2013.01)

(58) Field of Classification Search
CPC ................................................ A61F 13/26–28
See application file for complete search history.

(56) References Cited

U.S. PATENT DOCUMENTS

| | | |
|---|---|---|
| 3,645,263 A | 2/1972 | Bates |
| 3,765,416 A | 10/1973 | Werner et al. |
| 3,835,856 A | 9/1974 | Warncke |
| 4,361,150 A | 11/1982 | Voss |
| 4,479,791 A | 10/1984 | Sprague |
| 4,676,773 A | 6/1987 | Sheldon |
| 4,891,042 A | 1/1990 | Melvin et al. |

(Continued)

FOREIGN PATENT DOCUMENTS

| | | |
|---|---|---|
| CA | 945703 A | 4/1974 |
| CN | 1229351 A | 9/1999 |

(Continued)

OTHER PUBLICATIONS

Federal Service for Intellectual Property, Decision To Grant, Russian Application No. 2020115156, dated Aug. 27, 2020 (17 pages).

(Continued)

*Primary Examiner* — Susan S Su
(74) *Attorney, Agent, or Firm* — Cantor Colburn LLP

(57) ABSTRACT

An applicator for a tampon comprising an inner tube and an outer tube is provided. The inner tube is slideable within the outer tube and the applicator has a forward end. A plurality of petals are provided at the forward end of the inner tube and at least one protrusion is provided at the base of each petal. Each protrusion extends in a radially outward direction from the outer surface of the inner tube.

12 Claims, 5 Drawing Sheets

(56) References Cited

U.S. PATENT DOCUMENTS

| | | |
|---|---|---|
| 4,960,417 A | 10/1990 | Tarr et al. |
| 5,080,659 A | 1/1992 | Nakanishi |
| 5,571,540 A | 1/1996 | Weyenberg et al. |
| 5,554,109 A | 9/1996 | Frayman |
| 5,569,177 A | 10/1996 | Fox et al. |
| 6,019,744 A | 2/2000 | Altdorf et al. |
| D726,313 S | 4/2015 | Covers et al. |
| 10,918,515 B2 | 2/2021 | Callaghan et al. |
| 2003/0028138 A1 | 2/2003 | Karapasha et al. |
| 2003/0144639 A1 | 7/2003 | Gehling |
| 2005/0273043 A1 | 12/2005 | Osborn, et al. |
| 2007/0021708 A1* | 1/2007 | Bertulis ............ A61F 13/266 604/15 |
| 2008/0154176 A1 | 6/2008 | Van Ingelgem et al. |
| 2008/0195029 A1 | 8/2008 | Van Ingelem et al. |
| 2009/0192436 A1 | 7/2009 | Karapasha et al. |
| 2010/0016780 A1 | 1/2010 | VanDenBogart et al. |
| 2010/0324468 A1 | 12/2010 | Gann et al. |
| 2011/0201992 A1 | 8/2011 | Smet et al. |
| 2011/0273727 A1 | 11/2011 | Seki et al. |
| 2016/0296380 A1 | 10/2016 | Graham et al. |

FOREIGN PATENT DOCUMENTS

| | | |
|---|---|---|
| CN | 101155568 A | 4/2008 |
| CN | 101346114 A | 1/2009 |
| CN | 102088942 A | 6/2011 |
| CN | 102341080 A | 2/2012 |
| CN | 103384508 A | 11/2013 |
| CN | 206007475 U | 3/2017 |
| CN | 201780094572.2 | 8/2020 |
| CN | 201780094573.7 | 8/2020 |
| CN | 201780094581.1 | 8/2020 |
| EP | 1695680 A1 | 8/2006 |
| EP | 1704841 A1 | 9/2006 |
| EP | 2404585 A1 | 1/2012 |
| GB | 2220359 A | 1/1990 |
| JP | 2013111180 A | 6/2013 |
| RU | 2406473 C2 | 12/2010 |
| WO | 90011747 A1 | 10/1990 |
| WO | 9711747 A1 | 4/1997 |
| WO | 2007115091 A1 | 10/2007 |
| WO | 2010046478 A1 | 4/2010 |
| WO | 2016156403 A1 | 10/2016 |

OTHER PUBLICATIONS

Federal Service for Intellectual Property, Decision To Grant, Russian Application No. 2020115119, dated Aug. 14, 2020 (18 pages).
Federal Service for Intellectual Property, Decision To Grant, Russian Application No. 2020115036, dated Aug. 14, 2020 (18 pages).
China National Intellectual Property Administration, Office Action, Application No. 201780094581.1, dated Aug. 10, 2020 (8 pages).
China National Intellectual Property Administration, Office Action, Application No. 201780094573.7, dated Aug. 7, 2020 (10 pages).
China National Intellectual Property Administration, Office Action, Application No. 201780094572.2, dated Aug. 7, 2020 (11 pages).
International Search Report and Written Opinion for International Application No. PCT/EP2017/075541, dated Feb. 12, 2018, 11 pages.
Applicants' related U.S. Appl. No. 16/649,245, dated Sep. 2, 2020.
Applicants' related U.S. Appl. No. 16/652,240, dated Sep. 15, 2020.
Applicants' related U.S. Appl. No. 16/652,281, dated Sep. 17, 2020.
International Preliminary Report on Patentability for International Application No. PCT/EP2017/075539, dated Sep. 16, 2019, 12 pages.
International Search Report and Written Opinion for International Application PCTEP2017/075539, dated Jan. 25, 2018, 11 pages.
International Preliminary Report on Patentability for International Application No. PCT/EP2017/075542, dated Sep. 18, 2019, 11 pages.
International Search Report and Written Opinion for International Application PCT/EP2017/075542, dated Feb. 14, 2018, 9 pages.
International Preliminary Report on Patentability for International Application No. PCT/EP2017/075543, dated Sep. 18, 2019, 13 pages.
International Search Report and Written Opinion for International Application PCT/EP2017/075543, dated Feb. 14, 2018, 8 pages.
China National Intellectual Property Administration, Second Office Action, Application No. 201780094581.1, dated Apr. 8, 2021 (22 pages).

* cited by examiner

SECTION A-A

SECTION B-B

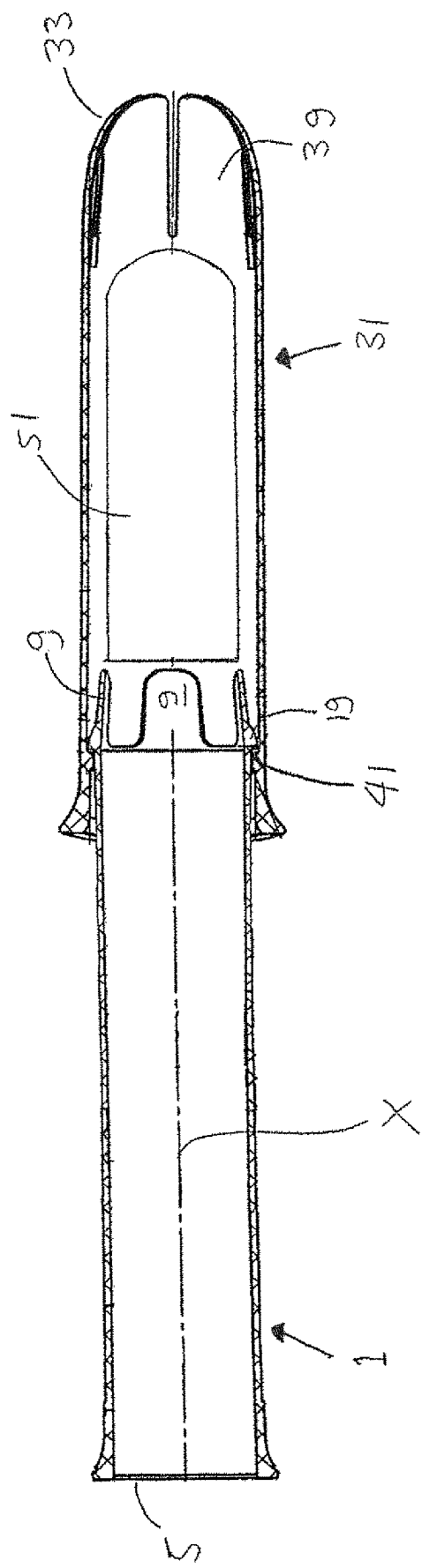

TAMPON APPLICATOR

CROSS REFERENCE TO RELATED APPLICATIONS

This is a U.S. National Phase application of PCT/EP2017/075541, filed Oct. 6, 2017, the disclosure of which is incorporated herein by reference in its entirety for all purposes.

TECHNICAL FIELD

The present disclosure relates to tampon applicators.

BACKGROUND

Tampons are female hygiene absorbent products used to absorb menstrual blood flow within the body of a user. Tampons may be provided with or without applicators. When no applicator is provided, the tampon is generally inserted manually by the user. However many women prefer to use an applicator to facilitate insertion of the tampon and/or for hygiene reasons.

Known tampon applicators generally include two cylindrical tubes arranged in a telescopic relationship with each other, one tube being slideable within the other tube. In one arrangement, the tampon is provided within the outer tube whilst the inner tube is provided within the outer tube behind the tampon and extending outside of the outer tube in a rearward direction. In use, the user inserts the outer tube into the body and pushes the rearwardly extending portion of the inner tube in a forward direction towards the tampon, and the front part of the inner tube makes contact with and pushes the tampon out of the outer tube and into the body of the user. It will be appreciated that, as the inner tube is only partially inserted into the outer tube, such applicators are relatively bulky.

In another arrangement, where the applicators may be referred to as "compact" or "collapsible" applicators, the tampon is located in the inner tube and the inner tube is almost entirely contained within the outer tube. This provides a more compact and discreet applicator. In such applicators, in use, the user first pulls an exposed rear part of the inner tube in a rearward direction so that the inner tube slides rearwardly with respect to the outer tube, thereby exposing most of the inner tube. Whilst the inner tube is being slid relative to the outer tube, the front end of the tampon may be engaged by the outer tube to help to hold the tampon in place whilst the inner tube is being rearwardly extended. In this manner, the tampon stays in position with respect to the outer tube whilst the inner tube slides backwards and extends rearwardly of the outer tube. This movement of the inner tube relative to the tampon and the outer tube results in the inner tube sliding in a rearward direction over the tampon and leaving the tampon within the outer tube. Once the tampon is no longer held within the inner tube and the inner tube is positioned rearwardly of the tampon, the outer tube may be inserted into the body of the user and the rearwardly extending portion of the inner tube may be pushed in a forward direction towards the tampon. The front part of the inner tube ideally then makes contact with the tampon and pushes the tampon out of the outer tube and into the body of the user.

As the tampon must fit within the inner tube and be readily slideable from the inner tube to the outer tube, the tampon is generally of a smaller diameter than the internal diameter of the inner tube. However, this can lead to the inner tube sliding back over and surrounding the tampon when the inner tube is pushed in a forward direction. This can prevent the tampon from exiting the applicator. In order to ensure that the inner tube does not slide back over the tampon but instead makes contact with the rear end of the tampon and pushes the tampon forwards out of the outer tube, users may angle the inner tube with respect to the outer tube when pushing the inner tube in a forward direction, so that the longitudinal axis of the inner tube and the longitudinal axis of the outer tube are no longer aligned or parallel. This usually permits the front end of the inner tube to make contact with the rear end of the tampon, but it complicates the process and requires more force from the user in order to expel the tampon from the applicator. Furthermore, it makes it more difficult for a user to correctly position a tampon within the body.

It would be desirable to provide an applicator that is of the compact type and which permits a user to more accurately, easily and comfortably insert a tampon into the body.

SUMMARY

According to the present disclosure there is provided an applicator for a tampon comprising an inner tube and an outer tube, the inner tube being slideable within the outer tube, the applicator having a forward end, wherein a plurality of petals are provided at the forward end of the inner tube and at least one protrusion is provided at the base of each petal, each protrusion extending in a radially outward direction from the outer surface of the inner tube.

The applicator may be of a compact type. The inner tube of the applicator may be configured to receive a tampon. The forward end refers to the front or distal end of the applicator, i.e. the part of the applicator which is inserted into the body. The rear or rearward end refers to the back or proximal end of the applicator, i.e. the part of the applicator which is not inserted into the body and which is handled by the user.

Each protrusion may extend from the base of a petal in the longitudinal direction of the inner tube towards the forward end of said petal.

The length of the protrusion in the direction of the longitudinal length of the inner tube may be at least a quarter of the distance between the base of the petal and the forward end of said petal.

The length of the protrusion in the direction of the longitudinal length of the inner tube may be greater than the width of the protrusion in a direction extending around the circumference of the inner tube. The protrusion may have a substantially constant width. Alternatively, the protrusion may have a width which tapers from the base of the petal (where the protrusion is at its widest) towards the forward end of the petal. The protrusion may have a substantially triangular shape in plan view (i.e. when viewed from directly above). The protrusion may have the shape of an isosceles triangle when viewed from above. The length of the protrusion may be greater than the width of the protrusion at the base of the petal.

A longitudinal section of the protrusion may have a substantially triangular shape, whereby the rear end of the protrusion may extend in a substantially radial direction outwardly from the outer surface of the inner tube and the hypotenuse of the triangle may extend from the rear end of the protrusion to its forward end, the forward end of the protrusion meeting the outer surface of the petal.

The forward end of each petal may be substantially 'U'-shaped. The petals may have a curved forward end or alternatively may have a straight forward end. The petals may be approximately semi-circular, "U"-shaped, square shaped or rectangular shaped.

One single protrusion may be provided at the base of each petal. Alternatively more than one protrusion may be provided at the base of each petal.

There may be two or more petals provided. Four petals may be provided. Alternatively six or eight petals may be provided.

The plurality of petals may be evenly spaced around the circumference of the inner tube. Each petal may be separated from adjacent petals by a gap. The gap may extend from the base of the petals to the forward end of the petals. The gap may have a width which extends in a direction around the circumference of the inner tube. The petals may each have a width which extends in a direction around the circumference of the inner tube. The width of the gap may be substantially constant along the longitudinal length of the gap. The gap may widen at its forward end if the petals taper to a rounded shape at their forward end. The gap may have a width which is greater than, the same as, or less than the width of the petals. The gap may have a width at the base of the petals which is similar to the width of the petals at the base of the petals.

The inner surface of the outer tube may comprise an annular protruding ring at or near to its rear end.

The internal diameter of the outer tube at the location of the annular protruding ring may be smaller than the external diameter of the inner tube including the protrusions such that the protrusions on the outer surface of the inner tube may be configured to engage with the annular protruding ring of the outer tube to thereby prevent the inner tube from sliding completely out of the outer tube at the rear end of the outer tube.

The inner tube and the outer tube may be formed from a thermoplastic material, such as a medical device classified thermoplastic material for example. The inner and outer tube may be formed from low density polyethylene (LDPE). The inner tube may be formed from a more rigid material or a stiffer material than the outer tube. For example, the outer tube may be formed from LDPE and the inner tube may be formed from polypropylene (PP). This permits the outer tube to be formed from a softer and/or more resilient material than the inner tube so that the outer tube is more comfortable when inserted into the body of a user. The inner tube may be formed of a more rigid or stiffer material to assist in pushing the tampon out from the outer tube of the applicator into the body of a user.

The applicator may further comprise a tampon disposed in the inner tube.

The applicator may comprise or consist of an inner tube and an outer tube and a tampon disposed in the inner tube.

BRIEF DESCRIPTION OF DRAWINGS

The present invention will now be described by way of example only and with reference to the following drawings, of which:

FIG. 8 shows a longitudinal cross-sectional view through a tampon applicator in accordance with an embodiment of the invention.

DETAILED DESCRIPTION OF PARTICULAR EMBODIMENTS

Figure 1:
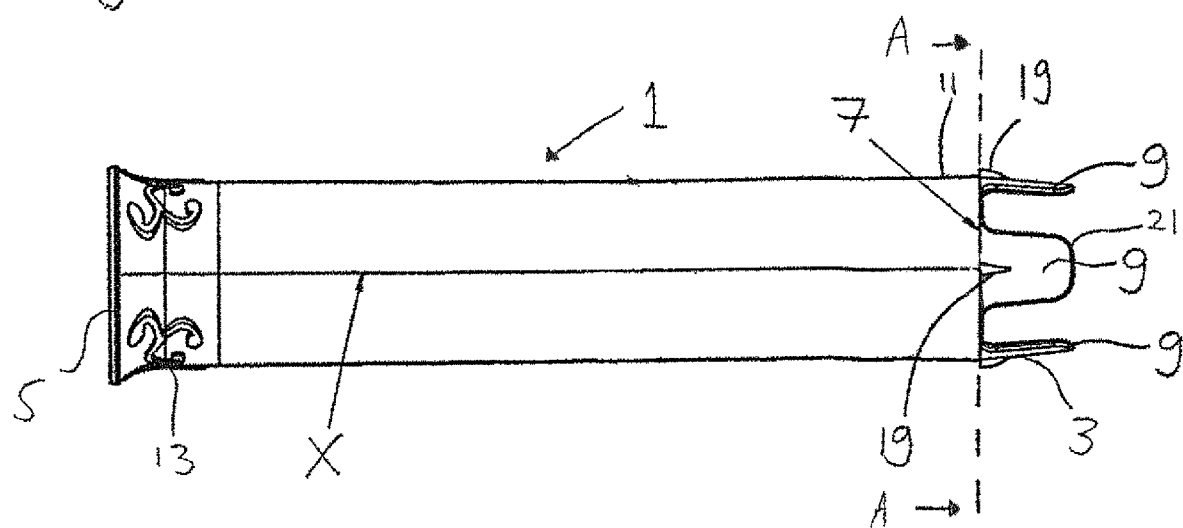
FIG. 1 is a side view of an inner tube of a tampon applicator in accordance with an embodiment of the invention.
Figure 2:
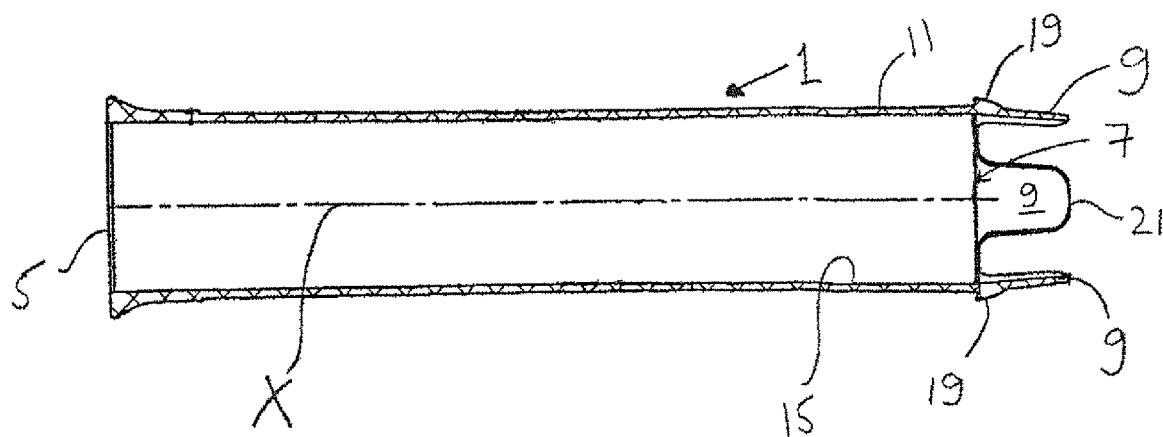
FIG. 2 is a longitudinal cross-sectional view through the inner tube of FIG. 1.

An inner tube 1 of a tampon applicator is shown in FIGS. 1 and 2. The direction along the longitudinal axis of the inner tube is shown as X. The inner tube 1 has a front end 3 and a rear end 5. The front end 3 of the inner tube 1 includes a plurality of petals 9. In this depicted embodiment, four identical petals are provided, the petals being evenly spaced around the circumference of the inner tube. In other embodiments, the petals may not be identical, and/or may not be spaced evenly around the circumference of the inner tube. It is advantageous to provide at least two petals. In embodiments of the invention two, three, four, five, six or more petals may be provided.

A protrusion 19 is provided at the base 7 of each petal 9. In this depicted embodiment, a single protrusion 19 is provided at the base 7 of each petal 9. However, in other embodiments two or more protrusions may be provided at the base of each petal.

The protrusions extend in a radially outward direction from the outer surface 11 of the inner tube 1. Each protrusion 19 extends from the base 7 of a petal 9 in the longitudinal direction X of the inner tube towards the forward end 21 of the petal 9. The length of the protrusion 19 in the longitudinal direction X may be at least a quarter of the distance between the base 7 of the petal 9 and the forward end 21 of the petal 9, and may be a third or even a half of this distance.

Figure 4:
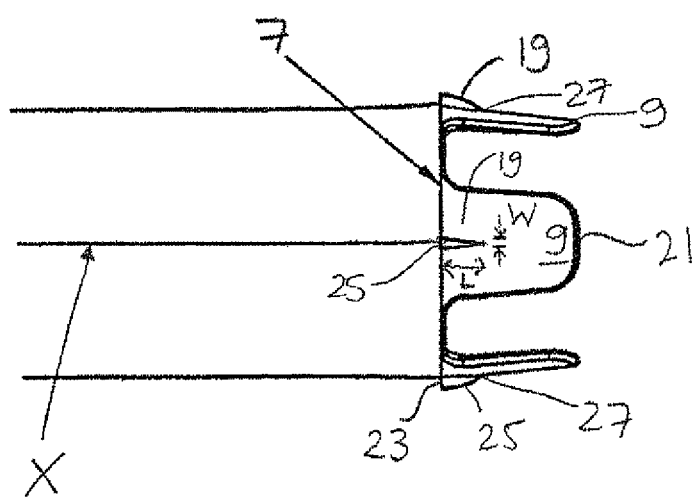
FIG. 4 is an enlarged side view of the forward part of the inner tube of FIG. 1.

The protrusions 19 have a width W in a direction extending around the circumference of the inner tube 1 (as shown in FIG. 4). The protrusions 19 may have a width which tapers from the base 7 of the petal 9 (where the protrusion 19 is at its widest) towards the forward end 21 of the petal 9 giving the protrusions 19 a triangular shape as shown in FIG. 1. Alternatively, the protrusions 19 may have a substantially constant width W giving the protrusions 19 a rectangular shape when viewed from directly above.

The protrusions 19 cause the petals 9 to bend inwards so that the forward end 3 of the inner tube has a tapered shape in the region of the petals 9, as can be seen in FIGS. 1 and 2. A tapered inner tube front end 3 may be beneficial for engaging with the rear end of a tampon and in pushing the tampon out of an outer tube of an applicator.

The rear end 5 of the inner tube 1 may be tapered such that the rear end 5 of the inner tube 1 is wider than the remainder of the inner tube 1. This may assist in preventing the inner tube from being pushed entirely within an outer tube. The rear end 5 of the inner tube may include decorative or grip features 13 which may assist a user to firmly grip the rear end 5 of the inner tube 1 between their fingers, thereby facilitating use of the applicator.

Figure 3:
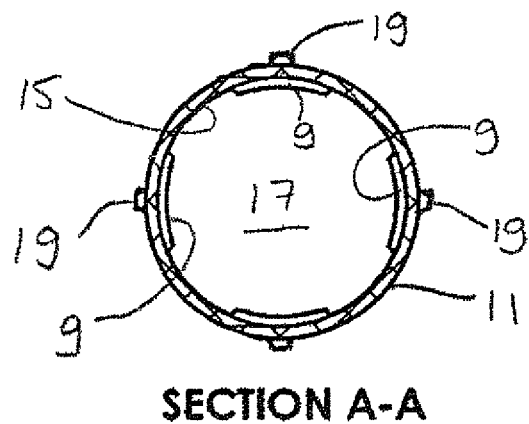
FIG. 3 shows a cross-section through the inner tube of FIG. 1 at the position A-A.

FIG. 3 shows a cross-section through the inner tube at the position shown as A-A in FIG. 1. The inner tube 1 defines an interior space 17 for receiving a tampon. The inner tube 1 has an inner surface 15 and an outer surface 11. The protrusions 19 and petals 9 can be seen in FIG. 3.

FIG. 4 shows an enlarged view of the forward part of the inner tube of FIG. 1. From FIG. 4 it can be seen that, in this depicted embodiment, the length L of the protrusions 19 in the longitudinal direction X is greater than the maximum width W of the protrusions in a direction extending around the circumference of the inner tube. In other embodiments, the length L may be equal to the width W or less than the width W. Where the applicator includes an outer tube having spikes protruding from the interior surface of the outer tube or from the interior surface of petals of the outer tube in order to hold a tampon in position whilst the inner tube is being moved rearwardly relative to the outer tube, it may be advantageous to provide protrusions 19 on the inner tube where the length L of the protrusions is greater than their width W. This is because protrusions having a smaller width W are less likely to become undesirably engaged with the spikes of the outer tube than protrusions having a larger width W. Providing protrusions having a tapered width may further help in preventing the spikes from engaging with the protrusions.

The protrusions 19 in the depicted embodiment have a substantially triangular shape. In other embodiments, the protrusions 19 may have another shape, such as rectangular or square shaped, for example. In the depicted embodiment, the rear end surface 23 of the protrusion 19 extends in a substantially radial direction outwardly from the outer surface 11 of the inner tube 1, such that the angle between the rear end surface 23 of the protrusion 19 and the outer surface 11 of the inner tube 1 is approximately 90 degrees. This is advantageous where the outer tube is provided with an interior annular ring, rim or protrusion as explained with reference to FIG. 8. The hypotenuse surface 25 of the depicted triangular protrusion extends from the radially most distant part of the rear end surface 23 of the protrusion 19 to the forward end 27 of the protrusion 19, the forward end 27 of the protrusion 19 meeting the outer surface of the petal 9. In this embodiment, the hypotenuse surface 25 has a curved shape as can be seen in FIG. 4. This may assist the inner tube to slide in a forwards direction relative to the outer tube during insertion of a tampon into the body of a user. In other embodiments, the hypotenuse surface 25 of the protrusion 19 may be a flat sloping surface rather than a curved one.

Figure 5A:
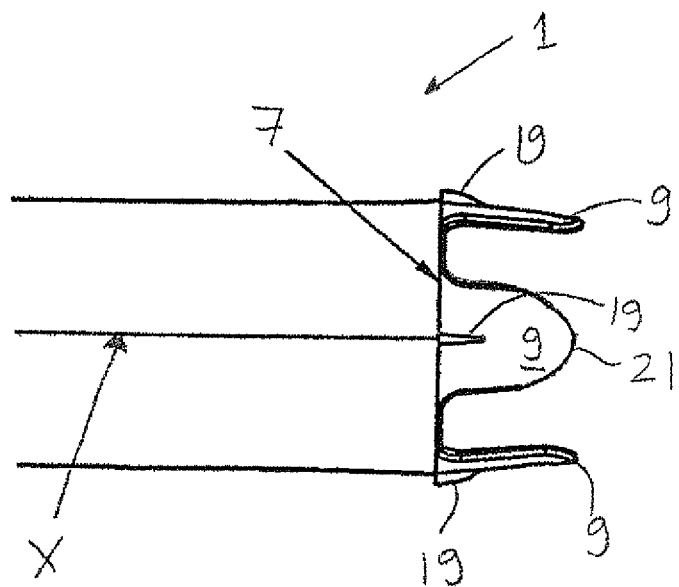
FIG. 5 shows alternative inner tube petal shapes.
Figure 5B:
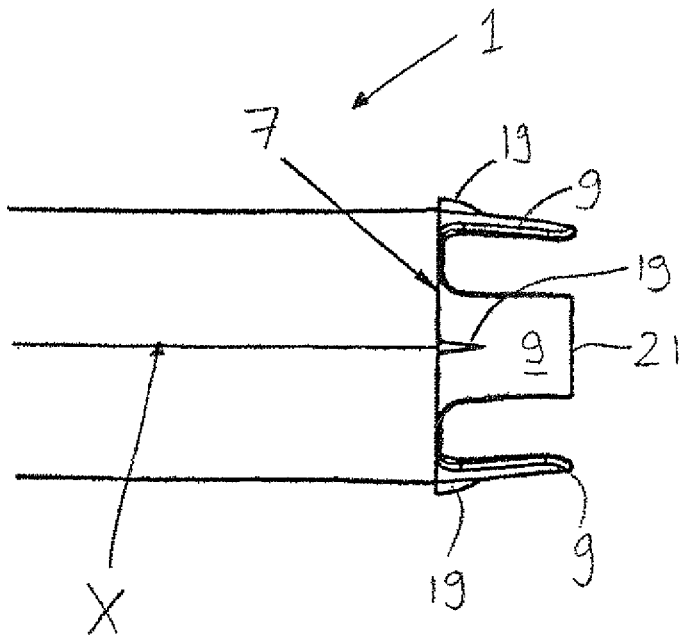

The petals 9 depicted in FIG. 4 are substantially "U"-shaped. However, the petals 9 may instead be of a rectangular or square shape, or may have a more rounded shape than that depicted in FIG. 4. FIG. 5a shows an inner tube 1 including petals 9 having a rounded forward end 21. FIG. 5b shows an inner tube 1 including petals 9 having a rectangular shape and having a forward end 21 that is not rounded. It may be advantageous to provide a relatively blunt or only gently rounded forward end 21 of the petal 9, such as that shown in FIG. 4, so that the forward end 21 of the petal 9 presents a reasonably large pushing surface for pushing a tampon out of the outer tube and into the body of a user. In this manner the applied force can be distributed over a greater area and there is less risk of the forward end 21 of the petal 9 breaking or becoming entangled with or embedded in the tampon.

Figure 6:
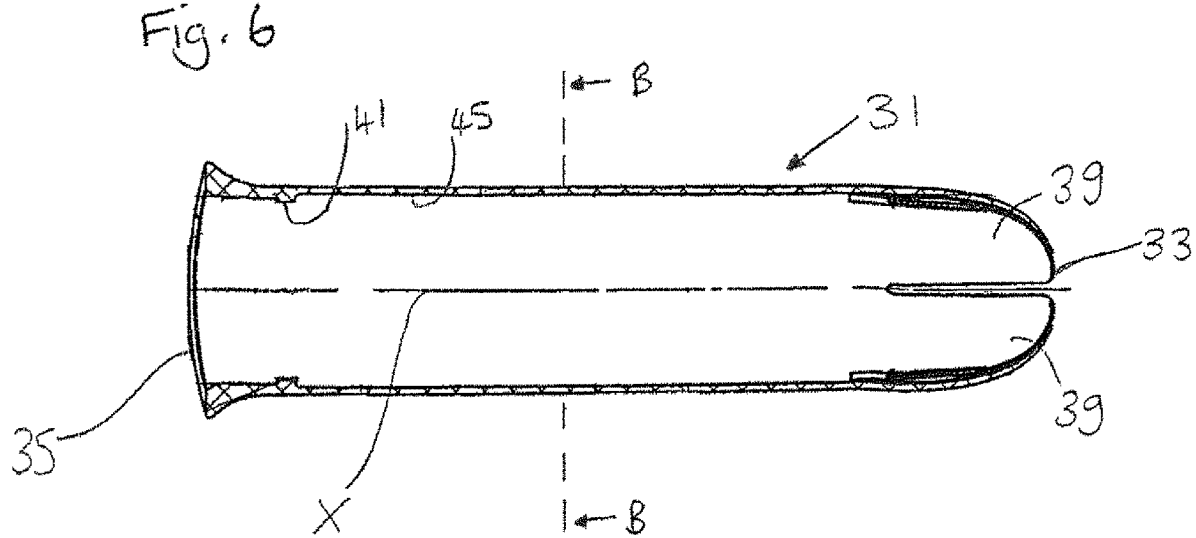
FIG. 6 is a longitudinal cross-sectional view through an outer tube of a tampon applicator in accordance with an embodiment of the invention.
Figure 7:
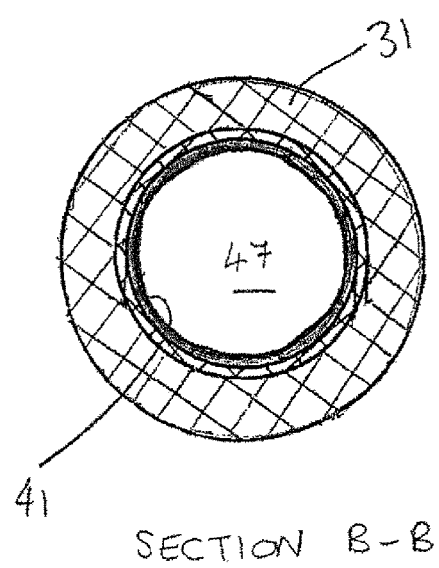
FIG. 7 is a cross-section through the outer tube of FIG. 6 at the position B-B.

A longitudinal section through an outer tube 31 is shown in FIG. 6. The outer tube 31 has a forward end 33 and a rear end 35. In this embodiment, the outer tube 31 includes a plurality of petals 39 at its forward end 33. Towards the rear end 35 of the outer tube 31 there is an annular protrusion 41 which extends circumferentially around the interior surface 45 of the outer tube 31 and which protrudes radially inwards into the interior space 47 defined by the outer tube 31, as can be seen in FIG. 7.

The internal diameter of the outer tube is slightly greater than the external diameter of the inner tube, to enable the inner tube to slide within the outer tube. Initially, a tampon is at least partly located within the inner tube and the inner tube is almost entirely located within the outer tube, except for the rearmost part of the inner tube. To use the applicator, a user grips the rearmost part of the inner tube and slides the inner tube backwards relative to the outer tube. Means, such as spikes provided on the interior forward end of the outer tube, hold the tampon in position relative to the outer tube whilst the inner tube slides relative to the outer tube. This allows the inner tube to slide rearwardly away from the tampon and to leave the tampon in the outer tube 31. The inner tube 1 is then positioned behind the tampon 51 as shown in FIG. 8.

The internal diameter of the outer tube at the location of the annular protrusion 41 is smaller than the external diameter of the protrusions 19 (i.e. the external diameter of the inner tube at the location of the protrusions 19), such that the protrusions 19 of the inner tube engage the annular protrusion 41 of the outer tube to prevent the inner tube from sliding backwards completely out of the outer tube.

The annular protrusion 41 of the outer tube may extend radially inwardly substantially at a right angle from the interior surface 45 of the outer tube 31. This may help to retain the inner tube 1 in the outer tube 31, particularly when the rear end surfaces 23 of the protrusions 19 extend radially outwardly at substantially right angles to the longitudinal direction X of the inner tube.

While the foregoing description and drawings represent exemplary embodiments of the present invention, it will be understood that various additions, modifications and substitutions may be made therein without departing from the spirit and scope of the present invention. In particular, it will be clear to those skilled in the art that the present invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components and otherwise, used in the practice of the invention, which are particularly adapted to specific environments and operative requirements without departing from the principles of the present invention. The presently disclosed embodiments are therefore to be considered in all respects as illustrative and not restrictive, the scope of the invention being indicated by the appended claims, and not limited to the foregoing description.

The invention claimed is:

1. An applicator for a tampon comprising an inner tube and an outer tube, the inner tube being slideable within the outer tube, the applicator having a forward end, wherein a plurality of petals are provided at a forward end of the inner tube and at least one protrusion is provided on and at a base of at least one petal, the at least one protrusion extending in a radially outward direction from an outer surface of the inner tube, wherein a length of the at least one protrusion in the direction of a longitudinal length of the inner tube is at least a quarter of a distance between the base of the at least one petal and a forward end of the at least one petal.

2. The applicator for a tampon in accordance with claim 1 wherein the at least one protrusion extends from the base of the at least one petal in a longitudinal direction of the inner tube towards a forward end of the at least one petal.

3. The applicator for a tampon in accordance with claim 1 wherein the length of the at least one protrusion in the direction of the longitudinal length of the inner tube is greater than a width of the at least one protrusion in a direction extending around a circumference of the inner tube.

4. The applicator for a tampon in accordance with claim 1 wherein a forward end of the at least one petal is substantially 'U'-shaped.

5. The applicator for a tampon in accordance with claim 1 wherein one single protrusion is provided at a base of the at least one petal.

6. The applicator for a tampon in accordance with claim 1 wherein four petals are provided.

7. The applicator for a tampon in accordance with claim 1 wherein the plurality of petals are evenly spaced around a circumference of the inner tube.

8. The applicator for a tampon in accordance with claim 1 wherein an inner surface of the outer tube comprises an annular protruding ring at or near to its rear end.

9. The applicator for a tampon in accordance with claim 8 wherein an internal diameter of the outer tube at the location of the annular protruding ring is smaller than an external diameter of the inner tube including the at least one protrusion such that the at least one protrusion on the outer surface of the inner tube is configured to engage with the annular protruding ring of the outer tube to thereby prevent the inner tube from sliding completely out of the outer tube at a rear end of the outer tube.

10. The applicator for a tampon in accordance with claim 1, wherein the applicator further comprises a tampon disposed in the inner tube.

11. An applicator for a tampon comprising an inner tube and an outer tube, the inner tube being slideable within the outer tube, the applicator having a forward end, wherein a plurality of petals are provided at a forward end of the inner tube and at least one protrusion is provided on and at a base of at least one petal, the at least one protrusion extending in a radially outward direction from an outer surface of the inner tube, wherein a longitudinal section through the at least one protrusion has a substantially triangular shape, a rear end of the at least one protrusion extending in a substantially radial direction outwardly from the outer surface of the inner tube and a hypotenuse of a triangle extending from the rear end of the at least one protrusion to its forward end, the forward end of the at least one protrusion meeting an outer surface of the at least one petal.

12. An applicator for a tampon comprising an inner tube and an outer tube, the inner tube being slideable within the outer tube, the applicator having a forward end, wherein a plurality of petals are provided at a forward end of the inner tube and at least one protrusion is provided on and at a base of at least one petal, the at least one protrusion extending in a radially outward direction from an outer surface of the inner tube, wherein the at least one protrusion has a width in a direction extending around a circumference of the inner tube, and wherein the width of the at least one protrusion tapers from the base of the at least one petal, where the at least one protrusion is at its widest, towards a forward end of the at least one petal.

* * * * *